United States Patent [19]

Frazier et al.

[11] Patent Number: 5,468,407
[45] Date of Patent: Nov. 21, 1995

[54] DIALKYLBENZENE MONOSULFONATE COLLECTORS USEFUL IN ORE FLOTATION

[75] Inventors: Kevin A. Frazier; Juan M. Garces; Guo-shuh J. Lee, all of Midland, Mich.

[73] Assignee: The Dow Chemical Company, Midland, Mich.

[21] Appl. No.: 333,659

[22] Filed: Nov. 3, 1994

[51] Int. Cl.$^6$ ................................................. B03D 1/02
[52] U.S. Cl. ........................... 252/61; 562/91; 562/94
[58] Field of Search ....................... 562/91, 94; 252/61

[56] References Cited

U.S. PATENT DOCUMENTS

| | | | |
|---|---|---|---|
| 3,169,987 | 2/1965 | Bloch | 260/505 |
| 4,298,547 | 11/1981 | Young | 260/505 A |
| 4,301,317 | 11/1981 | Young | 585/455 |
| 4,592,783 | 6/1986 | Dressler et al. | 106/14.05 |
| 5,004,841 | 4/1991 | Lee et al. | 568/678 |
| 5,015,367 | 5/1991 | Klimpel et al. | 209/166 |
| 5,026,933 | 6/1991 | Blain et al. | 585/7 |
| 5,173,176 | 12/1992 | Klimpel et al. | 209/166 |
| 5,243,116 | 9/1993 | Lee et al. | 585/467 |

FOREIGN PATENT DOCUMENTS

| | | |
|---|---|---|
| 0469940 | 2/1992 | European Pat. Off. . |
| 9300317 | 1/1993 | WIPO . |

*Primary Examiner*—José G. Dees
*Assistant Examiner*—Joseph M. Conrad, III

[57] ABSTRACT

A composition comprising a mixture of dialkylbenzene monosulfonic acids or salts thereof containing greater than about 60 weight percent of the para dialkylbenzene isomer and greater than about 80 weight percent of the combined di(2-alkyl)benzene and di(3-alkyl)benzene isomers. The composition exhibits improved properties as a mineral collector in ore flotation.

7 Claims, No Drawings

5,468,407

DIALKYLBENZENE MONOSULFONATE COLLECTORS USEFUL IN ORE FLOTATION

BACKGROUND OF THE INVENTION

This invention pertains to chemical collectors and their use in the recovery of minerals by froth flotation.

Flotation is a process of treating a mixture of finely divided mineral solids, e.g., pulverulent ore, which are suspended in a liquid under process conditions such that a portion of the solids is separated from other finely divided mineral solids, e.g., silica, siliceous gangue, clays and other like materials present in the ore. The flotation process comprises introducing a gas (or providing a gas in situ) in the liquid to produce a frothy mass containing certain of the solids on the top of the liquid, and leaving suspended (unfrothed) other solid components of the ore. Flotation is based on the principle that introducing a gas into a liquid containing solid particles of different materials suspended therein causes adherence of some gas to certain suspended solids and not to others, and makes the particles having the gas adhered thereto lighter than the liquid. Accordingly, these particles rise to the top of the liquid to form a froth.

The minerals and their associated gangue which are treated by froth flotation generally do not possess sufficient hydrophobicity or hydrophilicity to allow adequate separation. Therefore, various chemical reagents, "collectors," are often employed in froth flotation to create or enhance the properties necessary to allow separation. Collectors are used to enhance the hydrophobicity and thus the floatability of different mineral values. Collectors must have the ability to (1) attach to the desired mineral species to the relative exclusion of other species present; (2) maintain the attachment in the turbulence or shear associated with froth flotation; and (3) render the desired mineral species sufficiently hydrophobic to permit the required degree of separation.

U.S. Pat. No. 5,173,176 generally discloses the techniques and problems associated with froth flotation and specifically discloses a process for recovering oxide minerals by froth flotation in the presence of a chemical collector. The collector is taught to be a dialkylated aryl sulfonic acid, such as, di(dodecyl)benzene sulfonic acid or a salt thereof. Preferred dialkylated aryl sulfonic acids are disclosed to contain one $C_{1-3}$ alkyl substituent and one $C_{10-24}$ alkyl substituent. Examples of this preferred type of collector include hexadecylcumene monosulfonic acid and octadecylcumene monosulfonic acid.

Dialkylated aryl sulfonic acids and their salts can be obtained commercially. Commercial samples are known to be prepared by traditional Friedel-Crafts or liquid acid technologies. For example, it is known to dialkylate benzene with an alkylating agent, such as an olefin, in the presence of a Friedel-Crafts reagent, such as aluminum chloride, or a liquid acid, such as phosphoric acid. The resulting dialkylated benzene can then be sulfonated with traditional sulfonating reagents, such as sulfur trioxide or sulfuric acid, to yield the corresponding dialkylbenzene monosulfonic acid. Disadvantageously, the alkylation step produces a mixture of ortho and para, and to a lesser extent meta, dialkylated isomers. Additionally, the alkyl moiety can be attached to the phenyl ring at a variety of isomeric positions along the alkyl chain. For example, in 1,4-dioctylbenzene the octyl moiety can be attached at the 2-, 3- or 4-position along the chain. Consequently, dialkylated aryl monosulfonates which are produced using traditional Friedel-Crafts or liquid acid catalysts exist as mixtures of many isomers. U.S. Pat. No. 5,173,176 is silent with regard to distinguishing the individual efficiency of each of these isomers in ore flotation applications.

U.S. Pat. No. 4,301,317 and European patent publication no. 0,469,940 teach the monoalkylation of benzene with long chain olefins typically having from 6 to 20 carbon atoms in the presence of dealuminated acid mordenite catalysts. It is taught that a mixture of phenylalkanes enriched in the 2- and 3-phenylalkane isomers is produced. These patent documents also teach the sulfonation of the phenylalkane mixture to the corresponding phenylalkane sulfonates, but are silent with respect to dialkylation and the isomer distribution obtained therefrom.

U.S. Pat. No. 5,026,933 discloses a process wherein a lower olefin, such as propylene, is oligomerized to a mixture of substantially linear $C_{10+}$ olefins. Thereafter, it is taught that benzene can be alkylated with the linear $C_{10+}$ olefins in the presence of dealuminated acid mordenite to yield linear phenylalkanes enriched in the 2-phenylalkane isomer. The phenylalkanes are taught to be sulfonated with fuming sulfuric acid to the corresponding alkylbenzene sulfonates. This patent is silent with respect to dialkylation and the isomer distribution obtained therefrom.

U.S. Pat. No. 5,004,841 discloses the alkylation of benzene with an olefin having preferably up to eight carbon atoms to form dialkylated benzene enriched in the para isomer. The catalyst is taught to be a dealuminated acid mordenite which is prepared by heating an acid mordenite having a silica/alumina molar ratio less than 40/1 and a Symmetry Index, as determined by X-ray diffraction, between about 0.5 and 1.0, and thereafter treating the heated mordenite with strong acid so as to prepare the dealuminated acid mordenite catalyst characterized by a silica/alumina molar ratio greater than 50/1 and a Symmetry Index of at least about 1.0. This patent is silent with respect to alkylation by olefins having more than eight carbon atoms, is silent with respect to phenylalkane isomer distributions, and is silent with respect to sulfonation.

It would be beneficial to know which of the many isomers of the dialkylated aryl monosulfonates taught in U.S. Pat. No. 5,173,176 are the most efficient collectors for ore flotation applications. Selective use of the most efficient collectors would maximize the productivity of ore flotation processes.

Summary of the Invention

In one aspect, this invention is a composition comprising a novel isomeric mixture of dialkylbenzene monosulfonic acids or salts thereof. The mixture contains greater than about 60 weight percent of the para dialkylbenzene isomer and greater than about 80 weight percent of the combined di(2-alkyl)benzene and di(3-alkyl)benzene isomers. The para di(alkyl)benzene sulfonate isomer can be represented in its acid or salt forms by the formula shown in FIG. 1:

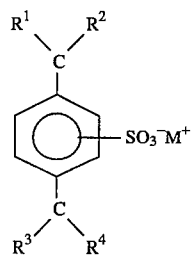

FIG. 1 wherein M may be a hydrogen ion, a metal ion with a valence of +1, ammonium ion, or a (hydrocarbyl)ammonium ion; and wherein $R^1$, $R^2$, $R^3$, and $R^4$ are each alkyl moieties such that the combined number of carbon atoms in $R^1$, $R^2$, $R^3$, and $R^4$ is equal to or greater than 10.

The novel composition of this invention is significantly enriched in the para di(2-alkyl)benzene and para di(3-alkyl)benzene isomers. As evidenced hereinbelow, 2,5-di(2-alkyl)benzene and 2,5-di(3-alkyl)benzene monosulfonic acids and the corresponding salts thereof unexpectedly exhibit improved efficiencies when used as collectors in ore flotation processes.

In a second aspect, this invention is an improved process for the recovery of minerals by froth flotation. The process comprises subjecting an aqueous slurry comprising particulate minerals selected from the group consisting of oxide ores, sulfide ores, noble metals, carbon based inks, and mixtures thereof to froth flotation in the presence of a collector for the minerals. The mineral collector comprises the novel isomeric mixture of dialkylated benzene monosulfonic acids or salts thereof identified hereinabove, which contain greater than about 60 percent by weight of the para dialkyl isomer and greater than about 80 percent by weight of the combined di(2-alkyl) and di(3-alkyl) benzene isomers. Advantageously, the method of this invention has been found to be superior to prior art ore flotation methods.

In a third aspect, this invention is a process of preparing the aforementioned novel mixture of dialkylated benzene monosulfonic acids or salts thereof enriched in the para dialkylated isomer and further enriched in the di(2-alkyl) and di(3-alkyl) benzene isomers. The process involves alkylation followed by sulfonation. The alkylation comprises contacting benzene or monoalkylbenzene with an olefin in the presence of a dealuminated acid mordenite zeolite under reaction conditions such that a mixture of dialkylated benzenes is formed containing greater than about 60 percent by weight para dialkylbenzene isomer and greater than about 80 percent by weight of the combined di(2-alkyl)benzene and di(3-alkyl)benzene isomers. Thereafter, the mixture of isomerically-enriched dialkylated benzenes is contacted with a sulfonating agent under reaction conditions such that the corresponding dialkylated benzene monosulfonic acids or salts thereof are formed. This method finds utility in the synthesis of improved collectors useful in ore flotation processes.

DETAILS OF THE INVENTION

The composition of this invention contains a mixture of predominantly 2,5-di(2-alkyl)benzene and 2,5-di(3-alkyl)benzene monosulfonic acids or salts thereof. The para dialkylated isomer typically comprises greater than about 60 weight percent, preferably greater than about 80 weight percent, and more preferably, greater than about 85 weight percent of the mixture. The 2-phenylalkane and 3-phenylalkane isomers combined typically comprise greater than about 80 weight percent, preferably, greater than about 85 weight percent, and more preferably, greater than about 90 weight percent of the composition. Heretofore, a composition of this increased isomeric enrichment was not known.

The p-di(alkyl)benzene monosulfonate composition of this invention may be generally represented in its acid or salt forms by FIG. 1, wherein $M^+$ is selected from the group consisting of hydrogen ion; monovalent metal ions, preferably Group IA metal ions, more preferably sodium ion; and ammonium ions represented by the formula $R_3NH^+$ wherein each R may be independently hydrogen, an alkyl or hydroxyalkyl radical, and preferably, a $C_{1-4}$ alkyl or a $C_{1-4}$ hydroxyalkyl radical. Illustrative $C_{4-1}$ alkyl radicals include methyl, ethyl, propyl, isopropyl, n-butyl, sec-butyl, and t-butyl. Illustrative $C_{1-4}$ hydroxyalkyl radicals include hydroxymethyl, hydroxyethyl, hydroxypropyl, and hydroxybutyl. Suitable ammonium ions include ammonium ($NH_4^+$), methylammonium, ethylammonium, dimethylammonium, trimethylammonium, hydroxyethylammonium and methylhydroxyethylammonium. Again in FIG. 1, the substituents $R^1$, $R^2$, $R^3$, and $R^4$ each represent alkyl moieties such that the combined number of carbon atoms in $R^1$, $R^2$, $R^3$, and $R^4$ is equal to or greater than 10. Preferably, the sum of the carbon atoms in $R^1$, $R^2$, $R^3$, and $R^4$ is equal to or greater than about 14, more preferably, equal to or greater than about 16. Preferably, the combined number of the carbon atoms in $R^1$, $R^2$, $R^3$, and $R^4$ is equal to or less than about 32, more preferably, equal to or less than about 26.

Suitable examples of the dialkylated benzene monosulfonic acids or salts of this invention include dihexylbenzene monosulfonic acid, dioctylbenzene monosulfonic acid, dinonylbenzene monosulfonic acid, didecylbenzene monosulfonic acid, didodecylbenzene monosulfonic acid, hexyl dodecylbenzene monosulfonic acid, hexadecylcumene monosulfonic acid, octadecylcumene monosulfonic acid, and the corresponding salts of these compounds, including the Group IA metal salts thereof, and the ammonium salts thereof. Preferably, the composition comprises a dialkylbenzene monosulfonic acid or salt thereof wherein one alkyl substituent is a $C_{3-8}$ alkyl and wherein the second alkyl substituent is a $C_{9-24}$ alkyl. More preferably, the composition is hexadecylcumene monosulfonic acid or octadecylcumene monosulfonic acid, or the corresponding salts thereof; most preferably, hexadecylcumene monosulfonic acid.

The preparation of monosulfonated species is critical to the practice of this invention; however, the presence of disulfonated species is not thought to be detrimental from a theoretical standpoint as long as at least about 80 weight percent of the monosulfonated species is present. Typically, this concentration of monosulfonates is easily achieved. Dialkylbenzenes sulfonate readily to the monosulfonate, but the latter do not readily disulfonate. Preferably, at least about 90 weight percent of the monosulfonated species is present in the composition of this invention, more preferably, at least about 95 weight percent of the monosulfonated species is present.

The composition of this invention can be prepared by a process which involves alkylating benzene or a monoalkylbenzene to a dialkylated benzene, and thereafter sulfonating the dialkylated benzene to the dialkylbenzene monosulfonic acid or salt. The process comprises contacting benzene or monoalkyl benzene with an olefin in the presence of a dealuminated acid mordenite zeolite under reaction conditions sufficient to form a mixture of dialkylated benzenes which is, as noted hereinbefore, enriched in the para dialkylated isomer and further enriched in the 2-phenylalkane and 3-phenylalkane isomers. Thereafter, the alkylation product stream is contacted with a sulfonating agent, such as sulfuric acid or sulfur trioxide, under reaction conditions sufficient to form the corresponding isomer enriched dialkylbenzene monosulfonic acid or salt thereof.

As noted hereinbefore, the combined number of carbon atoms in $R^1$, $R^2$, $R^3$, and $R^4$ of FIG. 1 is equal to or greater than 10. Since the alkyl substituents of FIG. 1 each contain an additional carbon atom not included in $R^1$, $R^2$, $R^3$ or R4, the total number of carbon atoms on the two alkyl substituents is therefore equal to or greater than 12. The carbon atoms of the alkyl substituents may be distributed symmetrically such that both alkyl moieties contain the same number of carbon atoms. Alternatively, the carbon atoms may be distributed asymmetrically such that one alkyl moiety contains fewer carbon atoms than the other. For example, one alkyl moiety may contain only three carbon atoms, whereas the second alkyl moiety may contain nine or more carbon atoms. An asymmetrical distribution is preferred for ore flotation applications, more preferably, an asymmetrical distribution in which one substituent is a $C_{3-8}$ alkyl and the second substituent is a $C_{9-24}$ alkyl.

In order to prepare a symmetrical dialkylated benzene, the alkylation feedstream should contain benzene and an olefinic alkylating agent. The olefinic alkylating agent may be any aliphatic olefin having six or more carbon atoms. Preferably, a $C_{8-32}$ olefin is employed, more preferably, a $C_{8-18}$ olefin. Suitable olefinic alkylating agents include hexenes, heptenes, octenes, nonenes, decenes, dodecenes, hexadecenes, octadecenes, and higher homologues of these. The olefinic bond may be at any location along the aliphatic chain. Typically, olefins obtained commercially exist predominantly as the 1-alkene isomer, and therefore, this isomer is preferred for the process of the invention. The more preferred olefinic alkylating agents for generating symmetrical dialkylated benzenes include 1-hexene, 1-octene, 1-decene, and 1-dodecene, most preferably, 1-octene and 1-decene.

In order to prepare an asymmetrical dialkylated benzene, a monoalkylbenzene may be obtained commercially and then alkylated with an olefin having a different number of carbon atoms from the alkyl substituent. A preferred monoalkylbenzene which is commercially available is cumene. Alternatively, an unsymmetrical dialkylated benzene can be prepared by contacting benzene with a first olefin under reaction conditions such that a monoalkylbenzene is formed, and thereafter, contacting the monoalkylbenzene with a second olefin under reaction conditions such that an unsymmetrical dialkylated benzene is formed. As an example, the first alkylating agent could be propylene, butene, hexene or octene, thereby producing respectively cumene, butylbenzene, hexylbenzene, or octylbenzene. The second olefin would be a long chain olefin, preferably, having 9 or more carbon atoms, more preferably, having from 9 to about 24 carbon atoms. Suitable examples include nonenes, decenes, dodecenes, hexadecenes, octadecenes, and higher homologues of these. Preferably, the first olefin is a $C_{3-8}$ olefin and the second olefin is a $C_{9-24}$ olefin. More preferably, the first olefin is propylene, and the second olefin is a $C_{16-22}$ olefin. Most preferably, the first olefin is propylene and the second olefin is hexadecene or octadecene. As noted above, any isomer or isomeric mixture of the olefin is suitable, but typical commercial olefins contain the 1-alkene isomer predominantly.

Any acid mordenite zeolite may be used as the alkylation catalyst in the alkylation step of this invention, provided that the novel dialkylated benzene of the invention is formed containing greater than about 60 weight percent para dialkyl isomer and greater than about 80 weight percent of the combined di(2-alkyl)benzene and di(3-alkyl)benzene isomers. A preferred acid mordenite catalyst and its preparation are described in U.S. Pat. No. 5,004,841, incorporated herein by reference. The preferred mordenite is characterized as having a silica/alumina molar ratio of at least 50:1, a Symmetry Index defined hereinafter of at least about 1.0, and a porosity such that the total pore volume is in the range from about 0.18 cc/g to about 0.45 cc/g, and the ratio of the combined meso- and macropore volume to the total pore volume is in the range from about 0.25 to about 0.75. For the purposes of this invention, a micropore has a radius in the range of about 3 Angstrom (Å) units to 10 Å; a mesopore has a radius in the range of 10 Å to 100 Å; and a macropore has a radius in the range of 100 Å to 1000 Å.

The preparation of the preferred acid mordenite catalyst, as described in U.S. Pat. No. 5,004,841, involves selecting a starting acid mordenite having a silica/alumina molar ratio of less than 40:1 and a Symmetry Index, as determined by X-ray diffraction, of between about 0.5 and about 1.3, preferably between about 0.7 and about 1.3. The Symmetry Index is a dimensionless number obtained from the X-ray diffraction pattern of sodium or acid mordenite, as measured in the hydrated form. The Symmetry Index is defined as the sum of the peak heights of the [111] (13.45, 2Θ) and [241](23.17 2Θ) reflections divided by the peak height of the [350] (26.25 2Θ) reflection.

The starting acid mordenite may be obtained commercially, or alternatively, may be prepared by slurrying a sodium mordenite having the required silica/alumina molar ratio and Symmetry Index with an inorganic or organic acid under conditions such that the sodium ions are exchanged for hydrogen ions. Preferred acids include hydrochloric acid, sulfuric acid, phosphoric acid, nitric acid, acetic acid, and oxalic acid, with the inorganic acids being more preferred. Typically, the acid concentration ranges from about 0.01N to about 6.0N, preferably from about 0.5N to about 3.0N. Preferably, the ratio of acid to mordenite ranges from about 5 to about 10 cc acid solution per gram mordenite. The slurrying treatment is conducted at a temperature between about 10° C. to about 100° C. for about 5 to about 60 minutes. After the initial acid treatment, the mordenite typically is washed with water and dried at a temperature between about 20° C. and about 150° C.

Following the exchange with acid and drying in air, the acidic mordenite zeolite is calcined in air or heated in an inert atmosphere, such as nitrogen. Preferably, the temperature of the calcination or heating is in the range from about 300° C. to about 800° C., more preferably, from about 500° C. to about 750° C., most preferably, from about 650° C. to about 750° C.

After calcining, the mordenite is subjected to an additional acid treatment for the purpose of further dealumination. The second acid treatment comprises contacting the calcined mordenite with a strong acid under conditions sufficient to produce the acidic mordenite catalyst used in this invention. The strong acid is typically an inorganic acid, such as, nitric acid, hydrochloric acid, or sulfuric acid. The concentration of the acid in aqueous solution preferably ranges from about 2N to about 15N, more preferably, from about 4N to about 12N, and most preferably from about 6N to about 8N. The ratio of aqueous acid solution to mordenite is in the range from about 3 to about 10, preferably about 5, cc acid solution per gram mordenite. The mordenite is contacted with the strong acid at a temperature between about 22° C. and about 220° C. for from about 1 to about 6 hours. The heat treatment and strong acid treatment steps can be repeated more than once, if desired. The acid-treated mordenite is thereafter washed with water and dried for several hours at 100° C. to 150° C. Prior to use in the alkylation process, the mordenite catalyst is activated by calcining for about 2 hours at a temperature between about 300° C. and about 800° C.

After the original sodium mordenite is treated with acid, calcined, and retreated with strong acid according to the aforementioned preparation, a preferred acid mordenite catalyst is obtained which is capable of converting benzene in high yield to dialkylated benzene. The catalyst exhibits certain characteristics by which it may be identified, specifically, its silica/alumina molar ratio, Symmetry Index, and porosity.

As a result of the acid extractions, the silica/alumina molar ratio of the mordenite is increased to a value greater than 50:1. Preferably, the silica/alumina molar ratio is at least about 160:1, more preferably, at least about 175:1, even more preferably, at least about 190:1. Generally, the silica/alumina molar ratio is not higher than about 2500:1, more preferably, not higher than about 1000:1.

As a further result of the calcination and acid extractions, the Symmetry Index of the mordenite catalyst is increased over that of the original mordenite. A Symmetry Index of at least about 1.0 results in catalysts showing minimal deactivation. Preferably, the Symmetry Index ranges from about 1.0 to about 2.0. In addition, the total pore volume is in the range from about 0.18 cc/g to about 0.45 cc/g, and the ratio of the combined meso- and macropore volume to total pore volume is in the range from about 0.25 to about 75. The measurement of porosity is described in detail in U.S. Pat. No. 5,004,841, cited hereinabove.

Any alkylation process conditions may be employed so long as a dialkylated benzene is formed enriched, as noted before, in the para dialkylated isomer and further enriched in the di(2-alkyl)benzene and di(3-alkyl)benzene isomers. In a continuous mode of operation the weight hourly space velocity (WHSV) of the overall feed with respect to catalyst is preferably in the range from about 0.5 $hr^{-1}$ to about 100 $hr^{-1}$, more preferably, in the range from about 0.5 $hr^{-1}$ to about 20 $hr^{-1}$. The molar ratio of benzene or monoalkylated benzene to olefin is generally less than about 10:1 and greater than about 1:1. Preferably, the ratio of benzene or monoalkylated benzene to olefin is between about 1.7:1 and about 2.9:1, more preferably, between about 2.0:1 and about 2.7:1. Typically, the temperature is in the range from about 50° C. to about 300° C., preferably, in the range from about 80° C. to about 250° C. The pressure is typically in the range from about 1 bar to about 200 bar, preferably, in the range from about 1 bar to about 10 bar.

If benzene or monoalkylated benzene is contacted as described hereinabove with an olefinic alkylating agent in the presence of a suitable acid mordenite catalyst, a mixture of dialkylated benzenes is formed enriched in the para dialkylated isomer. Surprisingly, the predominant phenylalkane isomers are the 2-phenylalkane and the 3-phenylalkane isomers. The isomerically enriched mixture is thereafter monosulfonated by methods generally known in the art. Suitable sulfonating agents and sulfonation process conditions are set forth by E. A. Knaggs, M. L. Nussbaum, and A. Shultz, in "Sulfonation and Sulfation," *Kirk-Othmer Enclopedia of Chemical Technology*, 3rd ed., Volume 22, John Wiley and Sons, New York, 1983, pp. 1-45, which is incorporated herein by reference. Typical sulfonation conditions include the use of an excess of concentrated sulfuric acid or fuming sulfuric acid (oleum, $H_2SO_4+SO_3$) at a temperature ranging between about 0° C. and about 150° C. The monosulfonic acid can be converted to the sodium salt, for example, by neutralization with sodium hydroxide or sodium sulfite.

The improved froth flotation process of this invention is useful in the recovery of mineral values from a variety of ores, including oxide ores, sulfide ores, and mixtures thereof. The oxide or oxygen-containing minerals which may be treated by the practice of this invention include carbonates, sulfates, hydroxides, and silicates, as well as oxides. Non-limiting examples of oxide ores which may be floated using the practice of this invention preferably include iron oxides, copper oxides, phosphorus oxides, aluminum oxides, and titanium oxides. Other types of oxygen-containing minerals which may be floated include carbonates, such as calcite, apatite, or dolomite, and hydroxides, such as bauxite.

Non-limiting examples of specific oxide ores which may be collected by froth flotation using the process of this invention include those containing cassiterite, hematite, cuprite, vallerite, calcite, talc, kaolin, apatite, dolomite, bauxite, spinel, corundum, laterite, azurite, rutile, magnetite, columbite, ilmenite, smithsonite, anglesite, scheelite, chromite, cerussite, pyrolusite, malachite, chrysocolla, zincite, massicot, bixbyite, anatase, brookite, tungstite, uraninite, gummite, brucite, manganite, psilomelane, goethite, limonite, chrysoberyl, microlite, tantalite, topaz and samarskite. One skilled in the art will recognize that the froth flotation process of this invention will be useful for the processing of additional oxide ores including oxide ores wherein oxide is defined to include carbonates, hydroxides, sulfates, and silicates, as well as oxides.

The process of this invention is also useful in the flotation of sulfide ores. Non-limiting examples of sulfide ores which may be floated by the process of this invention include those containing chalcopyrite, chalcocite, galena, pyrite, sphalerite, molybdenite, and pentlandite.

Noble metals such as gold and silver and the platinum group metals, including platinum, ruthenium, rhodium, palladium, osmium, and iridium, may also be recovered by the practice of this invention. For example, such metals are sometimes found associated with oxide and/or sulfide ores.

In addition to the flotation of ores found in nature, the flotation process and collector composition of this invention are useful in the flotation of minerals from other sources. One such example is the waste material from various processes such as heavy media separation, magnetic separation, metal working and petroleum processing. These waste materials often contain minerals that may be recovered by the flotation process of the present invention. Another example is the recovery of a mixture of graphite ink and other carbon-based inks in the recycling of paper.

In the froth flotation process of this invention the dialkylbenzene monosulfonic acid or salt thereof (hereinafter referred to as the "collector") may be used in any concentration which gives the desired selectivity and recovery of the desired mineral values. In particular, the concentration used is dependent upon the particular mineral to be recovered, the grade of the ore to be subjected to the froth flotation process, and the desired quality of the mineral to be recovered.

Additional factors to be considered in determining dosage levels include the amount of surface area of the ore to be treated. As will be recognized by one skilled in the art, the smaller the particle size, the greater the surface area of the ore and the greater the amount of collector reagents needed to obtain adequate recoveries and grades. Typically, oxide mineral ores must be ground finer than sulfide ores and thus require very high collector dosages or the removal of the finest particles by desliming. Conventional processes for the flotation of oxide minerals typically require a desliming step to function with acceptable collector dosage levels. The collector of the present invention functions at acceptable dosage levels with or without desliming.

Preferably, the concentration of the collector is at least about 0.001 kg/metric ton. It is also preferred that the total concentration of the collector is no greater than about 5.0 kg/metric ton, and more preferred that it is no greater than about 2.5 kg/metric ton. In general, to obtain optimum performance from the collector, it is most advantageous to begin at low dosage levels and increase the dosage level until the desired effect is achieved. While the increases in recovery and grade obtained by the practice of this invention increase with increasing dosage, it will be recognized by those skilled in the art that at some point the increase in recovery and grade obtained by higher dosage is offset by the increased cost of the flotation chemicals. It will also be recognized by those skilled in the art that varying collector dosages are required depending upon the type of ore and other conditions of flotation. Additionally, the collector dosage required has been found to be related to the amount of mineral to be collected. In those situations where a small amount of a mineral is susceptible to flotation using the process of this invention, a very low collector dosage is needed due to the selectivity of the collector.

It has been found advantageous in the recovery of certain minerals to add the collector to the flotation system in stages. By staged addition, it is meant that a part of the collector dose is added; froth concentrate is collected; an additional portion of the collector is added; and froth concentrate is again collected. The total amount of collector used is preferably not changed when it is added in stages. This staged addition can be repeated several times to obtain optimum recovery and grade. The number of stages in which the collector is added is limited only by practical and economic constraints. Preferably, no more that about six stages are used.

An additional advantage of staged addition is related to the ability of the collector of the present invention to differentially float different minerals at different dosage levels. As discussed above, at low dosage levels, one mineral particularly susceptible to flotation by the collector of this invention is floated while other minerals remain in the slurry. At an increased dosage, a different mineral may be floated thus permitting the separation of different minerals contained in a given ore.

In addition to the collector of this invention, other conventional reagents or additives may be used in the flotation process. Examples of such additives include various depressants and dispersants well-known to those skilled in the art. Additionally, hydroxy-containing compounds such as alkanol amines or alkylene glycols have been found to be useful in improving the selectivity to the desired mineral values in systems containing silica or siliceous gangue. The collector of this invention may also be used in conjunction with other collectors. In addition, frothers may be and typically are used. Frothers are well known in the art and reference is made thereto for the purposes of this invention. Examples of useful frothers include polyglycol ethers and lower molecular weight frothing alcohols.

A particular advantage of the collector of the present invention is that additional additives are not required to adjust the pH of the flotation slurry. The flotation process utilizing the collector of the present invention operates effectively at typical natural ore pH's ranging from about 5 or lower to about 9. This is particularly important when considering the cost of reagents needed to adjust slurry pH from a natural pH of around 7.0 or lower to 9.0 or 10.0 or above which is typically necessary using conventional carboxylic, sulfonic, phosphonic and xanthic collectors.

The ability of the collector of the present invention to function at relatively low pH means that it may also be used in those instances where it is desired to lower the slurry pH. The lower limit on the slurry pH at which the present invention is operable is that pH at which the surface charge on the mineral species is suitable for attachment by the collector.

Since the collector of the present invention functions at different pH levels, it is possible to take advantage of the tendency of different minerals to float at different pH levels. This makes it possible to do one flotation run at one pH to optimize flotation of a particular species. The pH can then be adjusted for a subsequent run to optimize flotation of a different species, thus facilitating separation of various minerals found together.

The collector of this invention may also be used in conjunction with conventional collectors. For example, the dialkylbenzene monosulfonic acids, or salts thereof, of this invention may be used in a two-stage flotation in which the dialkylbenzene monosulfonic acid or salt recovers primarily oxide minerals, while a second stage flotation using conventional collectors is used to recover primarily sulfide minerals or additional oxide minerals. When used in conjunction with conventional collectors, a two-stage flotation may be used wherein the first stage comprises the process of this invention and is done at the natural pH of the slurry. The second stage involves conventional collectors and is conducted at an elevated pH. It should be noted that in some circumstances, it may be desirable to reverse the stages. Such a two-stage process has the advantages of using less additives to adjust pH and also permits a more complete recovery of the desired minerals by conducting flotation under different conditions.

Additional details can be found in U.S. Pat. No. 5,173,176, pertaining to the types of minerals, additives, and process conditions which are suitable for the ore flotation method of this invention.

The following examples are provided to illustrate the invention and should not be interpreted as limiting it in any way. Unless stated otherwise, all parts and percentages are by weight.

The following examples include work involving Hallimond tube flotation and flotation done in laboratory scale flotation cells. It should be noted that Hallimond tube flotation is a simple way to screen collectors, but does not necessarily predict the success of collectors in actual flotation. Hallimond tube flotation does not involve the shear or agitation present in actual flotation and does not measure the effect of frothers. Thus, while a collector must be effective in a Hallimond tube flotation if it is to be effective in actual flotation, a collector effective in Hallimond tube flotation will not necessarily be effective in actual flotation. It should also be noted that experience has shown that collector dosages required to obtain satisfactory recoveries in a Hallimond tube are often substantially higher than those required in a flotation cell test. Thus, the Hallimond tube work cannot precisely predict dosages that would be required in an actual flotation cell.

EXAMPLE 1

(a) Preparation of acid mordenite catalyst: An acid mordenite catalyst having a silica/alumina molar ratio of 203 and a Symmetry Index of 1.83 is prepared as in U.S. Pat. No. 5,004,841. A sodium mordenite (300 g) having a silica/alumina molar ratio of 19 and a Index of 1.26 is ion-exchanged for 30 minutes with 3000 ml of an aqueous solution of 1M hydrochloric acid to yield the corresponding acid mordenite. The H-mordenite is washed with water and then calcined in air at 700° C. for 2 hr. The calcined mordenite is extracted with 6M nitric acid by using 5 cc acid solution per gram mordenite under reflux conditions for 6 hr to yield the dealuminated acid mordenite catalyst. The catalyst is calcined at 750° C. for 2 hr before use in the alkylation process.

(b) Preparation of p-(2-hexadecyl)cumene: Cumene (6.25 ml) is heated to reflux in a flask (250 ml) equipped with a magnetic stirrer, reflux condenser and inlet port. Dealuminated mordenite powder (0.5 g) prepared hereinabove is added all at once to the cumene. 1-Hexadecene (10.1 g) is added via pipet as the mixture is stirred. The reaction mixture is then maintained at 110°–120° C. for 24 hr. Thereafter, the mixture is cooled and filtered. The filtrate is distilled under reduced pressure to yield p-(2-hexadecyl) cumene (130° C./0.1 Hg;92 percent pure, based on gas chromatographic, GC, analysis). Other isomers, mainly p-(3-hexadecyl)cumene, comprise 8 percent of the composition.

(c) Preparation of 2,5-(2-hexadecyl)cumene monosulfonic acid: The p-(2-hexadecyl)cumene sample (2.5 g), prepared hereinabove, is placed in a 50 mL flask and cooled with an ice bath. Fuming sulfuric acid (ca. 30 percent, 0.5 mL) is added dropwise via pipet to the alkylate. The mixture is magnetically stirred during the addition, and stirring is continued for 10 min after the addition is complete. Analysis of the reaction mixture by high pressure liquid chromatography (HPLC) indicates that unsulfonated alkylate remains. Ten drops more of fuming sulfuric acid are added to complete the sulfonation. Anhydrous ether (10 mL) is added slowly to the cold reaction mixture followed by hexane (40 mL). The mixture is stirred vigorously for 5 min. Next, the acid layer is allowed to settle, and the hexane layer is collected by decantation. More hexane (ca. 40 mL) is added to the acid layer followed by stirring and decantation. This process is repeated twice more. The combined hexane fractions are evaporated under reduced pressure to provide crude 2,5(2-hexadecyl) cumene monosulfonic acid (2.47 g). The product is identified using HPLC, $^1$H and $^{13}$C nuclear magnetic resonance (NMR) spectroscopy, and fast atom bombardment mass spectrometry (FAB-MS); negative ion m/e 423 [M-HI]$^-$. The sulfonic acid is used for flotation experiments without further purification.

(d) Ore Flotation Test: A sample of apatite (1.1 g) sized to about −60 to +120 U.S. mesh is placed in a small bottle with 20 ml of deionized water. The mixture is shaken for 30 seconds and then the water phase containing some suspended fine solids or slimes is decanted. This desliming procedure is repeated two more times.

A 150-ml portion of deionized water is placed in a 250 ml glass beaker. Next, 2.0 ml of a 0.10 molar solution of potassium nitrate is added as a buffer electrolyte. The deslimed mineral is added along with deionized water to bring the total volume to about 180 ml. The 2,5-(2-hexadecyl)cumene monosulfonic acid sample prepared hereinabove (1 g) is added to Isopar M™ brand aliphatic hydrocarbon (Exxon, 100 g) to make a 1 percent solution. This solution (0.05 cc) is added to the mineral slurry, and the slurry is allowed to condition with stirring for 15 min while the pH is monitored.

The slurry is transferred into a Hallimond tube designed with a hollow needle fitted at the base of a 180 ml tube. After the addition of the slurry to the Hallimond tube, a vacuum of 5 inches of mercury is applied for a period of 10 min to an opening in the tube. The vacuum allows air bubbles to enter the tube through the hollow needle. During flotation, the slurry is agitated with a magnetic stirrer set at 200 revolutions per minute.

The floated and unfloated materials are filtered out of the slurry and oven dried at 100° C. Each portion is weighed and an "ore flotation ratio" is calculated. The ore flotation ratio is defined as that fractional portion of the original mineral, apatite in this example, which is placed in the Hallimond tube and recovered by flotation. Thus, an ore flotation ratio of 1.00 indicates that all of the material is recovered. When 2,5-(2-hexadecyl)cumene sulfonic acid is tested as an ore flotation collector, as described herein, an ore flotation ratio of 0.973±0.05 is achieved.

After each test all equipment is washed with concentrated hydrochloric acid and rinsed with 0.10 N sodium hydroxide and deionized water before the next run.

Comparative Experiment 1

An isomeric mixture of hexadecylcumenes is prepared by alkylating cumene with 1-hexadecene via conventional Friedel-Crafts alkylation (AlCl$_3$, 0° C., 30 min). The GC analysis of the alkylation product shows a large number of peaks which are consistent with the presence of many hexadecylcumene isomers. The mixture contains less than 60 percent para dialkyl isomer and less than 80 percent of the combined (2-hexadecyl)-cumene and (3-hexadecyl-)cumene isomers. The mixture is sulfonated using fuming sulfuric acid, according to the method described in Example 1. The product is characterized as hexadecylcumene monosulfonic acid by FAB-MS: negative ion m/e 423 [M-H]$^-$ The sulfonic acid mixture (0.05 cc of a 1 percent solution in Isopar M™) is tested as an ore collector on a sample of apatite according to the method of Example 1. An ore flotation ratio of 0.350 is measured. When Comparative Experiment 1 is compared with Example 1, it is seen that the 2,5-(2-hexadecyl)cumene monosulfonic acid of the invention achieves significantly better ore flotation recovery as compared with the isomeric mixture of hexadecylcumene sulfonates prepared by traditional Friedel-Crafts alkylation.

EXAMPLE 2

A sample of predominantly 2,5-(2-octadecyl)cumene monosulfonic acid is prepared in accordance with method of in Example 1, with the exception that 1-octadecene is employed as the alkylating agent instead of 1-hexadecene. The sample contains 91.2 percent of the p-(2-octadecyl-)cumene isomer and 7.2 percent of the p-(3-octadecyl-)cumene isomer, as determined by GC analysis of the alkylate. The product is characterized as octadecylcumene monosulfonic acid by $^1$H and $^{13}$C NMR and FAB-MS: negative ion m/e 451 [M-HI]$^-$. The sample is tested as an ore flotation collector according to the method of Example 1, and an ore flotation ratio of 0.806 is measured.

Comparative Experiment 2

An isomeric mixture of octadecylcumenes is prepared by alkylating cumene with 1-octadecene by conventional Friedel-Crafts alkylation (AlCl$_3$, 0° C. 30 min). A GC analysis of the alkylation product shows a large number of peaks which are consistent with a large number of octadecylcumene isomers. The mixture contains less than 60 percent para dialkyl isomer and less than 80 percent combined (2-octadecyl)cumene and (3-octadecyl)cumene isomers. The mixture is sulfonated using fuming sulfuric acid, according to the method described in Example 1. The product is characterized as octadecylcumene monosulfonic acid by FAB-MS: negative ion m/e 451 [M-H]$^-$.

The isomeric mixture of sulfonates is tested as an ore collector according to the method of Example 1, and an ore flotation ratio of 0.402 is measured. When Comparative Experiment 2 is compared with Example 2, it is seen that 2,5-(2-octadecyl)cumene monosulfonic acid of the invention is a far superior ore flotation collector than the isomeric mixture of octadecylcumene sulfonic acids prepared by Friedel-Crafts methods.

EXAMPLE 3 p-Di(2-decyl)benzene is prepared according to the method of Example 1, with the exception that 1-decene is used as the alkylating agent in place of hexadecene. Analysis by $^1$H NMR shows essentially pure p-di(2-decyl)benzene with no other isomers being detected. The alkylation product is sulfonated according to the method of Example 1. The sulfonation product is identified as 2,5-di(decyl)benzene monosulfonic acid, as determined by $^1$H and $^{13}$C NMR and FAB-MS: negative ion m/e 437 [M-H]$^{31}$.

The sulfonic acid is added to water to form a 1 percent solution, which is then used in a manner similar to that of Example 1 to evaluate the sulfonic acid as an ore collector. Flotation tests for apatite and hematite give an ore flotation ratio of 0.978 and 0.814, respectively, at a 0.05 cc dose.

Comparative Experiment 3

An isomeric mixture of di(decyl)benzenes is prepared by alkylating benzene with 1-decene via traditional Friedel-Crafts alkylation, as described in Comparative Experiment 1. A large number of isomers is obtained, as determined by GC analysis. The mixture contains less than 60 percent para dialkyl isomer and less than 80 percent of the combined (2-decyl)cumene and (3-decyl)cumene isomers. The di(decyl)benzene mixture is sulfonated with fuming sulfuric acid, as described in Experiment 1. The sulfonated product is identified as di(decyl)benzene monosulfonate, as determined by FAB-MS: negative ion m/e 437 [M-H]$^-$.

The isomeric mixture of sulfonates is tested as an ore collector by the method described in Example 3. An ore flotation ratio of 0.535 (0.05 cc dose) is measured for apatite. An ore flotation ratio of 0.653 (0.05 cc dose) is measured for hematite. When Comparative Experiment 3 is compared with Example 3, it is seen that 2,5-di(2-decyl)benzene monosulfonic acid is a significantly better ore collector than the isomeric mixture of di(decyl)benzene sulfonates prepared by traditional Friedel-Crafts methods.

EXAMPLE 4 p-Di(2-octyl)benzene is prepared by the method of Example 1, with the exception that 1-octene is used as the alkylating agent in place of 1-hexadecene. The alkylation product is distilled under reduced pressure to yield p-di(2-octyl)benzene (160°–162° C./1.2 mm Hg; 94.4 percent pure, based on GC analysis). The isomer is sulfonated using the method of Example 1 to yield 2,5-di(2-octyl)benzene monosulfonic acid, which is converted to the sodium salt by neutralization with sodium hydroxide. Analysis of the sulfonated product by HPLC and FAB-MS verifies the formation of 2,5-di(2-octyl)benzene monosulfonate (FAB-MS: m/e 381, [M-H]$^-$).

What is claimed is:

1. A composition comprising an isomeric mixture of dialkylbenzene monosulfonic acids or salts thereof, the mixture containing greater than about 60 weight percent of the para dialkylbenzene isomer and greater than about 80 weight percent of the combined di(2-alkyl)benzene and di(3-alkyl)benzene isomers, the para dialkylbenzene monosulfonic acid or salt being represented by the formula:

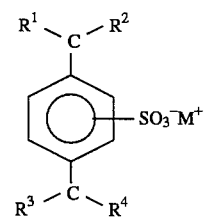

wherein M is a hydrogen ion, a metal ion having a valence of +1, ammonium ion, or a (hydrocarbyl)ammonium ion; and wherein $R^1$, $R^2$, $R^3$, and $R^4$ are each alkyl moieties such that the combined number of carbon atoms in $R^1$, $R^2$, $R^3$, and $R^4$ is equal to or greater than 10.

2. The composition of claim 1 wherein the para dialkylbenzene isomer is greater than about 80 weight percent and wherein the combined di(2-alkyl)benzene and di(3-alkyl)benzene isomers are greater than about 85 weight percent.

3. The composition of claim 1 wherein the combined number of carbon atoms in $R^1$, $R^2$, $R^3$, and $R^4$ ranges from a value equal to or greater than about 14 to a value equal to or less than about 32.

4. The composition of claim 1 wherein one alkyl substituent is a $C_{3-8}$ alkyl moiety and wherein the second alkyl substituent is a $C_{9-24}$ alkyl moiety.

5. The composition of claim 1 wherein the composition is selected from the group consisting of di(octyl)benzene monosulfonic acid, di(decyl)benzene monosulfonic acid, di(dodecyl)benzene monosulfonic acid, hexyl dodecylbenzene monosulfonic acid, hexadecylcumene monosulfonic acid, octadecylcumene monosulfonic acid, and the corresponding salts thereof.

6. The composition of claim 1 being prepared by a process comprising (A) contacting benzene or monoalkylbenzene with an olefin in the presence of an acid mordenite zeolite under reaction conditions sufficient to form a mixture of dialkylated benzenes wherein greater than about 60 weight percent of the mixture comprises the para dialkylated isomer, and wherein greater than about 80 weight percent of the mixture comprises the combined di(2-alkyl)benzene and di(3-alkyl)benzene isomers; and thereafter (B) contacting the mixture of dialkylated benzenes with a sulfonating agent under reaction conditions sufficient to form a mixture of the corresponding dialkylbenzene monosulfonic acids or salts thereof.

7. The composition of claim 6 wherein the acid mordenite zeolite is characterized as having a silica/alumina molar ratio greater than 50/1 and a Symmetry Index, as determined by X-ray diffraction, greater than about 1.0, the catalyst being prepared by
(1) heating an acid mordenite having a silica/alumina molar ratio less than 40/1 and a Symmetry Index between about 0.5 and about 1.3, and thereafter
(2) treating the heated mordenite with a strong acid under reaction conditions sufficient to remove an amount of alumina so as to prepare an acid mordenite zeolite having a silica/alumina molar ratio greater than 50/1, and
(3) optionally, repeating at least once the steps of (1) heating and (2) treating with strong acid so as to remove additional alumina.

* * * * *